United States Patent [19]

Roush et al.

[11] Patent Number: 4,960,884

[45] Date of Patent: Oct. 2, 1990

[54] PESTICIDAL 2-FLUOROETHYL ETHERS

[75] Inventors: David M. Roush, Princeton, N.J.; Donald A. Shaw, Philadelphia, Pa.; Michael L. Jones, Durham, N.C.; Jun H. Chang, Princeton Junction, N.J.

[73] Assignee: FMC Corporation, Philadelphia, Pa.

[21] Appl. No.: 399,448

[22] Filed: Aug. 28, 1989

Related U.S. Application Data

[63] Continuation of Ser. No. 318,437, Mar. 2, 1989, abandoned, which is a continuation of Ser. No. 64,278, Jun. 19, 1987, abandoned.

[51] Int. Cl.$^5$ ............. C07C 76/02; C07C 79/35; A01N 33/18
[52] U.S. Cl. ................. 514/721; 514/717; 514/718; 568/630; 568/645; 568/649; 568/655; 568/656; 568/658; 568/660; 568/661; 568/662; 568/663
[58] Field of Search ............ 568/588, 610, 649, 655, 568/656, 39, 630, 645, 649, 658, 660, 661, 662, 663; 562/474, 478, 467; 549/78; 514/717, 718, 721

[56] References Cited

U.S. PATENT DOCUMENTS

| | | | |
|---|---|---|---|
| 2,209,911 | 7/1940 | Bruson | 568/610 |
| 2,213,119 | 8/1940 | Britton | 568/610 |
| 3,766,247 | 10/1973 | Mendel | 562/467 |
| 4,552,894 | 11/1985 | Inoue et al. | 514/464 |

FOREIGN PATENT DOCUMENTS

| | | | |
|---|---|---|---|
| 2018248 | 4/1969 | Fed. Rep. of Germany | 568/588 |
| 0020549 | 2/1981 | Japan | 568/588 |
| 0157041 | 9/1984 | Japan | 568/655 |

OTHER PUBLICATIONS

Yoshimoto et al., "Chlorophenyl Carbamate Herbicide", Chem. Abstracts 88:100355e (1978).
Lahm & Drake, "Insecticidal 2-Fluoroethyl Ethers", Abstracts of Papers, 192nd ACS Meeting, Sep. 7-12, 1986, Abstract No. 43.
Ishida et al., Agr. Biol. Chem. 31, No. 6, 651–656 (1967).
Smirnova et al., "Synthesis of a Few Physiologically Active Substances", Chem. Abstracts 53:1243c (1958).
Smirnova et al., "Synthesis of Some β-Fluoroethyl Phenyl Esters", Chemical Abstracts 59:3804F (1963).
Smirnova et al., "Synthesis of 3-[α-(p-β-Fluoroethoxyphenyl)-β-Acetylethyl]-4-Hydroxycoumaxin . . .", Chem. Abstracts 58:4502a (1963).
Shigemitsu et al., "Fertilizers Containing Inhibitors of the Oxidation of Ammonium Salts to Nitrates", Chem. Abstracts 76:4519r (1972).

*Primary Examiner*—Alan Siegel
*Attorney, Agent, or Firm*—Robert L. Andersen; H. Robinson Ertelt

[57] ABSTRACT

Pesticidal mono-, di-, and tri-2-fluoroethyl ethers of the formula $R^1R^2{}_mAr(OCH_2CH_2F)_n$, compositions thereof and their insecticidal, acaricidal and nematicidal uses are described and claimed.

6 Claims, No Drawings

PESTICIDAL 2-FLUOROETHYL ETHERS

This application is a continuation, of application Ser. No. 318,437, filed Mar. 2, 1989 now abandoned which is a continuation of application Ser. No. 064,278 filed June 19, 1987 now abandoned.

The present invention relates to 2-fluoroethyl ethers useful for control of pests such as insects, acarids, and nematodes. More particularly the invention relates to 2-fluoroethyl aryl or arylmethyl ethers useful in controlling pests such as insects, nematodes and acarids in agricultural or horticultural crops. The invention comprises pesticidal compositions of such compounds, a method for control of such pests, and certain compounds which are themselves novel pesticides.

The pesticides of the present invention contain as the active component a compound of the general formula $R^1R^2{}_m Ar(OCH_2CH_2F)_n$ in which:

Ar is phenyl and n is 1 to 3, or Ar is naphthyl and n is 1 or 2, or Ar is phenylmethyl, (alkyl)(phenyl)methyl, diphenylmethyl, or naphthylmethyl and n is 1; and (a) m is 0 and $R^1$ is selected from hydrogen, halogen, alkyl, lower alkylcarbonyl(lower)alkyl, carboxyalkyl, halomethyl, hydroxymethyl, fluoroethoxymethyl, cyano, formyl, carboxyl, alkylcarbonyl, alkylaminocarbonyl, alkoxycarbonyl, aminocarbonyl, fluoroethoxycarbonyl, fluoroethoxyphenylcarbonyl, amino, lower alkylamino, di(lower)alkylamino, phenylmethanimido, nitro, alkoxy, difluoromethoxy, mercapto, methylthio, methylsulfinyl, methylsulfonyl, hydroxy, phenoxy, phenyl, fluoroethoxyphenyl, thienyl, or a group of the formula —OC(CH$_3$)$_2$CH$_2$— bridging adjacent carbon atoms of a phenyl ring, with the proviso that Ar is other than naphthyl when $R^1$ is carboxyl, alkoxycarbonyl, aminocarbonyl, methylthio, or hydroxy; or (b) m is 1, $R^1$ is selected from alkyl, halogen, cyano, nitro and fluoroethoxycarbonyl, and $R^2$ is selected from alkyl, halogen and nitro; or (c) m is 2–5, and $R^1$ methyl or halogen and $R^2$ is halogen.

In the foregoing and throughout the specification and claims, the following terms have the indicated meanings. "Alkyl", alone or modifying other groups, means a straight, branched, or cyclic alkane residue having from 1 to 6, preferably 1 to 4 carbon atoms. The term "halogen" or "halo" means bromine, chlorine, fluorine, or iodine. The term "lower alkyl" means an alkane residue of 1 to 3 carbon atoms, preferably 1–2 carbon atoms and "halomethyl" means a methyl group substituted with one or more halogen atoms.

Of the compounds referred to above, preferred insecticides are compounds of group (a) above in which $R^1$ is selected from hydrogen, cyano, nitro, methoxy, methylthio, methylsulfinyl, methylsulfonyl, or difluoroethoxymethyl. Preferred broad spectrum pesticides, i.e., those having insecticidal and nematicidal activity are compounds of group (a) above in which $R^1$ is selected from hydrogen, cyano, methoxy and fluoroethoxymethyl. Compounds having broad spectrum of nematicidal activity are compounds of group (a) which are unsubstituted diethers (i.e. n=2) or compounds of group (a) in which $R^1$ is selected from halogen, preferably bromo, phenyl, nitro or fluoroethoxyphenylcarbonyl, or compounds of group (b) in which $R^1$ is methyl and $R^2$ is chloro.

The examples below illustrate various methods for preparation of these compounds.

EXAMPLE 1

2-BROMOPHENYL 2-FLUOROETHYL ETHER

In a manner similar to that disclosed in German Offenlegungschrift DE No. 3,402,483, the reaction of 5.0 grams (0.029 mole) of 2-bromophenol, 6.0 grams (0.043 mole) of potassium carbonate, and 5.5 grams (0.03 mole) of 1-bromo-2-fluoroethane in 50 ml of N,N-dimethylformamide yielded 4.9 grams of 2-bromophenyl 2-fluoroethyl ether as an oil.

The nmr spectrum was consistent with the proposed structure.

EXAMPLE 2

4-(ETHYLAMINO)PHENYL 2-FLUOROETHYL ETHER

A solution of 3.0 grams (0.015 mole) of 4-acetamidophenyl 2-fluoroethyl ether in 15 ml of dry tetrahydrofuran was added dropwise to a stirred solution of 15 ml of a 3.4 M solution of sodium bis(2-methoxyethoxy)aluminium hydride (Red-Al ®) in toluene and 50 ml of dry tetrahydrofuran. The reaction mixture was stirred at room temperature for approximately 18 hours. The mixture was quenched with 1 ml of water and was filtered. The filtrate was evaporated under reduced pressure leaving a dark liquid which solidified upon standing. This solid was dissolved in ethyl acetate to which a small amount of water was added. A small amount of precipitate formed from which the organic solution was decanted. The organic solution was evaporated under reduced pressure leaving a dark liquid residue. This residue was purified by column chromatography on silica gel followed by distillation under reduced pressure to yield 1.6 grams of 4-(ethylamino)phenyl 2-fluoroethyl ether as a solid.

The nmr spectrum was consistent with the proposed structure.

EXAMPLE 3

2-FLUOROETHYL 2-DIFLUOROMETHOXYPHENYL ETHER

Step A 2-(2-Fluoroethoxy)phenyl formate

In a manner similar to that disclosed by Godfrey et al., (J. Chem. Soc. Perkin I, 1353–1354 (1974), the reaction of 10.0 grams (0.06 mole) of 2-(2-fluoroethoxy)benzaldehyde with 3-chloroperbenzoic acid (15.5 grams of 80–85% assay, 0.075 mole) in 250 ml of methylene chloride yielded 6.85 grams of 2-(2-fluoroethoxy)phenyl formate as an oil.

Step B 2-Fluoroethyl 2-difluoromethoxyphenyl ether

Chlorodifluoromethane was bubbled into a stirred solution of 6.6 grams (0.036 mole) of 2-(2-fluoroethoxy)-phenyl formate, 12.0 grams (0.215 mole) of potassium hydroxide, and 0.1 gram (0.00038 mole) of 18-crown-6 in 150 ml of tetrahydrofuran for 10 minutes. The resultant solution was heated at reflux for approximately 18 hours. The reaction mixture was cooled and was diluted with water. Evaporation of most of the solvent under reduced pressure left a solid residue. This residue was dissolved in a 3 N aqueous sodium hydroxide solution. The basic solution was extracted with three 100 ml portions of methylene chloride, and the extracts were combined. The extract was washed with an aqueous saturated sodium chloride solution. The washed extract was dried over anhydrous magnesium sulfate and filtered. The filtrate was evaporated under reduced pressure leaving a residue. This residue was purified by column chromatography on silica gel, eluting with diethyl ether:n-hexane(1:1), to yield 3.3 grams of 2-fluoroethyl 2-difluoromethoxyphenyl ether.

The nmr and ir spectra were consistent with the proposed structure.

EXAMPLE 4

2-FLUOROETHYL 2-METHYLSULFONYLPHENYL ETHER

A stirred mixture of 5.0 grams (0.027 mole) of 2fluoroethyl 2-methylthiophenyl ether and 9.3 grams (0.054 mole) of 3-chloroperbenzoic acid in 100 ml of diethyl ether was stirred at room temperature for two hours. The mixture was heated at reflux for four hours and was allowed to cool and stir at room temperature for approximately 18 hours. The reaction mixture was washed with an aqueous, 15% sodium hydroxide solution. The organic phase was dried over anhydrous potassium carbonate and filtered. The filtrate was evaporated under reduced pressure to yield 3.9 grams of 2-fluoroethyl 2-methylsulfonylphenyl ether as a solid, m.p. 67°-69° C.

The nmr spectrum was consistent with the proposed structure.

EXAMPLE 5

2-FLUOROETHYL 3-HYDROXYPHENYL ETHER

In a manner similar to that described by Godfrey et al., (J. Chem. Soc. Perkin I, 1353–1354 (1974), the reaction of 7.0 grams (0.042 mole) of 3-(2-fluoroethoxy)benzaldehyde with 3-chloroperoxybenzoic acid (14.0 grams of 75% technical, 0.061 mole) in 100 ml of dry methylene chloride followed by treatment with an aqueous, 15% sodium hydroxide solution and methanol yielded 5.0 grams of 2-fluoroethyl 3-hydroxyphenyl ether as an oil.

The nmr spectrum was consistent with the proposed structure.

EXAMPLE 6

4-(2-FLUOROETHOXYMETHYL)PHENYL 2-FLUOROETHYL ETHER

Step A 2-Fluoroethyl 4-hydroxymethylphenyl ether

A stirred solution of 7.0 grams (0.035 mole) of methyl 4-(2-fluoroethoxy)benzoate and 75 ml of a 1.0 M solution of diisobutylaluminium hydride in hexanes in 75 ml of toluene was heated at 40° C. for three hours. The mixture was cooled and quenched with methanol. This mixture was stirred at room temperature for approximately 18 hours and was filtered through a pad of celite. The filter cake was washed with a small amount of methanol. The combined filtrate was evaporated under reduced pressure to yield 5.0 grams of 2-fluoroethyl 4-hydroxymethylphenyl ether as an oil which slowly solidified.

Step B 4-(2-Fluoroethoxymethyl)phenyl 2-fluoroethyl ether

To a stirred solution of 5.0 grams (0.029 mole) of 2-fluoroethyl 4-hydroxymethylphenyl ether in 50 ml of tetrahydrofuran was added 15 ml of a 50% aqueous, sodium hydroxide solution, 7.6 grams (0.060 mole) of 1-bromo-2-fluoroethane, and 0.78 gram (0.0023 mole) of tetrabutylammonium hydrogen sulfate. The resultant mixture was stirred and heated at reflux for approximately 18 hours. The mixture was cooled and was extracted with diethyl ether. The extract was washed in succession with a dilute, aqueous, sodium hydroxide solution, an aqueous 10% lithium chloride solution, and a saturated, aqueous, sodium chloride solution. The washed organic phase was dried over anhydrous magnesium sulfate and filtered. The filtrate was evaporated under reduced pressure to leave an oil. Analysis of this oil by nmr indicated a large amount of starting material remained. The oil was again heated at reflux with the same quantities of the above reactants for 30 minutes. The reaction mixture was cooled and extracted with diethyl ether. The extract was washed several times with water followed by an aqueous, 15% lithium chloride solution. The washed extract was dried over anhydrous magnesium sulfate and filtered. The filtrate was evaporated under reduced pressure leaving an oil. Analysis of this oil by nmr indicated starting material was still present. This oil was heated at reflux with the same quantities of the above reagents for approximately 24 hours. The mixture was cooled and extracted with diethyl ether. The extract was washed with water and was dried over anhydrous magnesium sulfate and filtered. The filtrate was evaporated under reduced pressure to yield 1.9 grams of 4-(2-fluoroethoxymethyl)phenyl 2-fluoroethyl ether as an oil.

The nmr spectrum was consistent with the proposed structure.

EXAMPLE 7

2-FLUOROETHYL 4-MERCAPTOPHENYL ETHER

In a manner similar to Sugihara et al. (Synthesis, p 881 (1978)), the reaction of 8.7 grams (0.043 mole) of 2-fluoroethyl 4-methylsulfinylphenyl ether (Compound 80, prepared by the method of Example 4 using one equivalent of 3-chloroperbenzoic acid), 10.0 ml (0.086 mole) of 2,6-lutidine and 12.2 ml (0.086 mole) of trifluoroacetic anhydride in 160 ml of dry acetonitrile yielded 0.7 gram of 2-fluoroethyl 4-mercaptophenyl ether as an oil.

The nmr spectrum was consistent with the proposed structure.

EXAMPLE 8

4-CYANO-2-NITROPHENYL 2-FLUOROETHYL ETHER

In a manner similar to Sosnovsky et al. (Synthesis, p 722, (1979)), the reaction of 3.0 grams (0.014 mole) of -(2-fluoroethoxy)-3-nitrobenzaldehyde (prepared by the method of Example 1 from 4-hydroxy-3-nitrobenzaldehyde), 1.1 gram (0.015 mole) of hydroxylamine hydrochloride, and 1.2 ml (0.014 mole) of pyridine (dissolved in 10 ml of chloroform) in 50 ml of chloroform and ethanol (70/30 mixture) followed by treatment with 1.6 gram (0.014 mole) of selenium dioxide yielded 2.3 grams of 4-cyano-2-nitrophenyl 2-fluoroethyl ether as a solid.

The nmr spectrum was consistent with the proposed structure.

EXAMPLE 9

3-BROMOMETHYL-1,2-D (2-FLUOROETHOXY)BENZENE

Step A
1,2-Di(2-fluoroethoxy)-3-hydroxymethylbenzene

Under a dry nitrogen atmosphere a mixture of 6.0 grams (0.026 mole) of 2,3-di(2-fluoroethoxy)benzaldehyde (prepared by the method of Example 1 from 2,3-dihydroxybenzaldehyde) and 1.3 gram (0.034 mole) of sodium borohydride in 130 ml of ethanol was stirred at room temperature for approximately 18 hours. The reaction was quenched with dilute hydrochloric acid, and the mixture was extracted with diethyl ether. The extract was washed with dilute hydrochloric acid followed by an aqueous, saturated sodium chloride solution. The organic phase was dried over anhydrous magnesium sulfate and filtered. The filtrate was evaporated under reduced pressure to yield 5.4 grams of 1,2-di-(2-fluoroethoxy)-3-hydroxymethylbenzene as a solid.

Step B 3-Bromomethyl-1,2-di(2-fluoroethoxy)benzene

In a manner similar to that described by Noller et al. (Organic Synthesis, Vol. II. p 358-360), 2.0 grams (0.086 mole) of 1,2-di(2-fluoroethoxy)-3-hydroxymethylbenzene and 1.1 ml (0.0032 mole) of phosphorus tribromide were reacted in 90 ml of cold (0° C.) diethyl ether. The reaction mixture was partitioned between water and diethyl ether. The organic phase was washed with an aqueous, saturated sodium chloride solution. The washed organic phase was dried over anhydrous magnesium sulfate and filtered. The filtrate was evaporated under reduced pressure to yield 2.3 grams of 3-bromomethyl-1,2-di(2fluoroethoxy)benzene as a solid, mp 99°-100° C.

The nmr an ir spectra were consistent with the proposed structure.

EXAMPLE 10

3-(METHYLCARBONYLETHYL)-1,2-DI(2-FLUOROETHOXY)BENZENE

Step A
3-(methylcarbonylethenyl)-1,2-di(2-fluoroethoxy)benzene

To a stirred, cold (0° C.) solution of 5.2 grams (0.016 mole) 1-triphenylphosphoranylidene-2-propanone in 50 ml of dry tetrahydrofuran was added dropwise a solution of 3.4 grams (0.015 mole) of 2,3-di(2-fluoroethoxy)-benzaldehyde in 25 ml of dry tetrahydrofuran. After complete addition the reaction mixture was allowed to warm to room temperature and was then heated at reflux for three hours. The mixture was cooled to room temperature and stirred for approximately 18 hours. The solvent was removed by evaporation under reduced pressure leaving a residue. This residue was partitioned between diethyl ether and water. The organic phase was washed with an aqueous, saturated sodium chloride solution. The washed organic phase was dried over anhydrous magnesium sulfate and filtered. The filtrate was evaporated under reduced pressure leaving a brown residue. This residue was purified by column chromatography on silica gel, eluting with acetone:n-heptane (20:80), to yield 2.3 grams of 3-(methylcarbonylethenyl)-1,2-di(2-fluoroethoxy)benzene as a solid, mp 71°-72° C.

Step B
3-(Methylcarbonylethyl)-1,2-di(2-fluoroethoxy)benzene

Hydrogenation of 1.8 grams (0.0065 mole) of 3-(methylcarbonylethenyl)-1,2-di(2-fluoroethoxy)benzene with a catalytic amount of palladium (0.035 gram of 2% palladium on carbon) in ethanol yielded 1.8 gram of 3-(methylcarbonylethyl)-1,2-di(2-fluoroethoxy)benzene as a clear liquid.

The nmr and ir spectra were consistent with the proposed structure.

EXAMPLE 11

2,3-DI(2-FLUOROETHOXY)BENZAMIDE

Step A 2,3-Di(2-fluoroethoxy)benzoic acid

To a stirred solution of 3.0 grams (0.013 mole) of 2,3-di(2-fluoroethoxy)benzaldehyde in 10 ml of acetone was added 4.9 ml of a 2.6 M solution of aqueous chromic acid in acetone (Jones' reagent). The mixture was stirred at room temperature for 30 minutes, and the solvent was removed by evaporation under reduced pressure leaving a residue. This residue was dissolved in 30 ml of 1 N hydrochloric acid, and the acidic solution was extracted with five 30 ml portions of diethyl ether. The combined organic phase was extracted with three 35 ml portions of an aqueous, 10% sodium hydroxide solution. The basic extracts were combined and acidified. The acidic solution was extracted with five 30 ml portions of diethyl ether. The extracts were combined and washed with two 25 ml portion of an aqueous, saturated sodium chloride solution. The washed organic phase was dried over anhydrous magnesium sulfate and filtered. The filtrate was evaporated under reduced pressure leaving a solid residue. This solid was recrystallized from toluene to yield 1.4 gram of 2,3-di(2-fluoroethoxy)benzoic acid, mp 104°-105° C.

Step B 2,3-Di(2-fluoroethoxy)benzamide

A mixture of 1.3 gram (0.0054 mole) of 2,3-di(2-fluoroethoxy)benzoic acid, 1.0 gram (0.0080 mole) of oxalyl chloride, and one drop of N,N-dimethylformamide in 20 ml of diethyl ether was stirred at room temperature for approximately 18 hours. The solvent was evaporated from the reaction mixture leaving a residue. This residue was dissolved in 100 ml of methylene chloride, and the resulting organic solution was added slowly to a stirred, cold (0° C.) aqueous solution of ammonium hydroxide (5 ml of 30% solution). This mixture was allowed to warm to room temperature and stir for approximately 18 hours. The mixture was washed with an aqueous, sodium bicarbonate solution followed by an aqueous, saturated sodium chloride solution. The washed organic phase was dried over anhydrous magnesium sulfate and filtered. The filtrate was evaporated under reduced pressure leaving a solid residue. Recrystallization of this solid from a mixture of toluene and n-hexane yielded 0.6 gram of 2,3-di(2-fluoroethoxy)benzamide, mp 100°-101° C.

The nmr and ir spectra were consistent with the proposed structure.

EXAMPLE 12

ETHYL 2,3-DI(2-FLUOROETHOXY)BENZOATE

Under a dry nitrogen atmosphere 0.91 gram (0.0058 mole) of iodoethane was added dropwise to a stirred mixture of 1.2 gram (0.0049 mole) of 2,3-di(2-fluoroethoxy)benzoic acid (Compound 105) and 1.4 grams (0.0097 mole) of potassium carbonate in 40 ml of acetone. The reaction mixture was heated at reflux for 24 hours and then was allowed to cool to room temperature. The solvent was evaporated under reduced pressure leaving a residue. This residue was dissolved in diethyl ether, and the solution was washed with water followed by an aqueous, saturated sodium chloride solution. The washed organic phase was dried over anhydrous magnesium sulfate and filtered. The filtrate was evaporated under reduced pressure to yield 1.2 gram of ethyl 2,3-di(2-fluoroethoxy)benzoate as an oil, Compound 107 of Table 1.

The nmr and ir spectra were consistent with the proposed structure.

EXAMPLE 13

2-FLUOROETHYL 3,4-DI(2-FLUOROETHOXY)-5-NITROBENZOATE

Step A 2-Fluoroethyl 3,4-di(2-fluoroethoxy)benzoate

In a manner similar to Example 1, the reaction of 5.0 grams (0.032 mole) of 3,4-dihydroxybenzoic acid, 18.0 grams (0.13 mole) of potassium carbonate, and 12.3 grams (0.097 mole) of 1-bromo-2-fluoroethane in N,N-dimethylformamide yielded 5.0 grams of 2-fluoroethyl 3,4-di(2-fluoroethoxy)benzoate, as a solid.

Step B 2-Fluoroethyl 3,4-di(2-fluoroethoxy)-5-nitrobenzoate

The nitration of 5.0 grams (0.017 mole) of 2-fluoroethyl 3,4-di(2-fluoroethoxy)benzoate with 20 ml of concentrated nitric acid and three to five drops of concentrated sulfuric acid in 100 ml of glacial acetic acid yielded 3.9 grams of 2-fluoroethyl 3,4-di(2-fluoroethoxy)-5-nitrobenzoate as a solid.

The nmr spectrum was consistent with the proposed structure.

EXAMPLE 14

2,6-DI(2-FLUOROETHOXY)BENZOIC ACID

To a stirred solution of 3.0 grams (0.075 mole) of sodium hydroxide in 150 ml of ethanol was added 11.3 grams (0.039 mole) of 2-fluoroethyl 2,6-di(2-fluoroethoxy)benzoate (prepared by the method of Step A of Example 13 from 2,6-dihydroxybenzoic acid and three equivalents of 1-bromo-2-fluoroethane). The reaction mixture was stirred at room temperature for approximately 48 hours. The reaction mixture was filtered, and the filter cake was saved. The filtrate was evaporated under reduced pressure leaving a residue. The filter cake and residue were added to 200 ml of an aqueous, 10% hydrochloric acid solution. The resultant mixture was stirred at room temperature and was extracted with several portions of methylene chloride. The extracts were combined and dried over anhydrous magnesium sulfate. The dried organic phase was filtered, and the filtrate was evaporated under reduced pressure to yield 4.9 grams of 2,6-di(2-fluoroethoxy)benzoic acid as a solid, mp 57°–58° C.

The nmr spectrum was consistent with the proposed structure.

EXAMPLE 15

2-FLUOROETHYL 3-NITROBENZYL ETHER

Under a dry nitrogen atmosphere 1.1 gram (0.047 mole) of sodium metal was added to a stirred, cold (0° C.) solution of 3.0 grams (0.046 mole) of 2-fluoroethanol in 50 ml of dry tetrahydrofuran. After the sodium had dissolved, the solution was heated at reflux, and a solution of 5.0 grams (0.023 mole) of 3-bromomethylnitrobenzene in 10 ml of dry tetrahydrofuran was added dropwise. This mixture was heated at reflux for 24 hours and then was cooled. The reaction mixture was diluted with water, then was extracted with diethyl ether. The organic extract was washed with an aqueous, saturated, sodium chloride solution. The washed extract was dried over anhydrous magnesium sulfate and filtered. The filtrate was evaporated under reduced pressure leaving a residue. This residue was purified by column chromatography on silica gel, eluting with n-hexane:diethyl ether (4:1), to yield 0.8 gram of 2-fluoroethyl 3-nitrobenzyl ether as an oil.

The nmr and ir spectra were consistent with the proposed structure.

EXAMPLE 16

2-(2-FLUOROETHOXY)-1-HYDROXYMETHYLNAPHTHALENE

A solution of 2.5 grams (0.012 mole) of 2-(2-fluoroethoxy)-1-naphthaldehyde (prepared by the method of Example 1 from 2-hydroxy-1-naphthaldehyde) and 0.6 gram (0.015 mole) of sodium borohydride in 35 ml of ethanol was stirred at room temperature for 24 hours. The mixture was diluted with water and extracted with diethyl ether. The extract was dried over anhydrous magnesium sulfate and filtered. The filtrate was evaporated under reduced pressure to yield 1.2 gram of 2-(2-fluoroethoxy)-1-hydroxymethylnaphthalene as a solid.

The nmr and ir spectra were consistent with the proposed structure.

EXAMPLE 17

2-(2-FLUOROETHOXY)-6-(1-METHYLETHYL)-NAPHTHALENE

A solution of 0.92 grams (0.0074 mole) of 2-bromopropane in 5 ml of dry tetrahydrofuran was added to a stirred mixture of 0.9 gram (0.04 mole) of magnesium turnings. This mixture was heated to initiate the reaction. A solution of 3.68 grams (0.0296 mole) of 2-bromopropane in 20 ml of dry tetrahydrofuran was added dropwise to the mixture. After complete addition the reaction mixture was stirred and heated at reflux for one hour. The reaction mixture was cooled, and the solution was decanted from the unreacted magnesium. The decanted liquid was added dropwise to a stirred slurry of 5.0 grams (0.037 mole) of zinc chloride in 15 ml of dry tetrahydrofuran. This mixture was stirred at room temperate for one hour. To this slurry was added 0.5 gram (0.004 mole) of tetrabis(triphenylphosphine)palladium and a solution of 2.5 grams (0.0093 mole) of 6-bromo-2-(2-fluoroethoxy)naphthalene (Compound 157, prepared by the method of Example 1 from 6-bromo-2hydroxynaphthalene) in 20 ml of dry tetrahydrofuran. The reaction mixture was stirred and heated at 50° C. for approximately 18 hours. The mixture was hydrolyzed with 100 ml of a 1 N aqueous hydrochloric acid solution. This mixture was extracted with three 200 ml portions of diethyl ether. The extracts were combined and washed with water. The washed extract was dried over anhydrous magnesium sulfate and filtered. The filtrate was evaporated under reduced pressure leaving an orange oil which solidified upon standing. This solid was purified by column chromatography on silica gel, eluting with n-hexane:diethyl ether (4:1) to yield 0.85 gram of 2-(2-fluoroethoxy)-6-(1-methylethyl)naphthalene as a solid, mp 46°–48° C.

The nmr and ir spectra were consistent with the proposed structure.

EXAMPLE 18

2-FLUOROETHYL DIPHENYLMETHYL ETHER

To a stirred solution of 2.0 grams (0.011 mole) of benzhydrol in 15 ml of diethyl ether was added 4.0 ml (0.068 mole) of 2-fluoroethanol followed by the dropwise addition of 0.5 ml of concentrated sulfuric acid. The reaction mixture was stirred at room temperature for 24 hours. The reaction mixture was extracted with diethyl ether. The organic extract was washed with water followed by an aqueous, saturated sodium bicarbonate solution. The washed extract was dried over anhydrous magnesium sulfate and filtered. The filtrate was evaporated under reduced pressure to yield 2.0 grams of 2-fluoroethyl diphenylmethyl ether as a liquid.

The nmr spectrum was consistent with the proposed structure.

The compounds set forth below were prepared in accordance with the methods illustrated in the foregoing examples.

TABLE 1

| Cmpd No. | Name | M.P. (°C.) B.P. (°C./mm) |
|---|---|---|
| 1 | 2-Fluoroethyl phenyl ether | 21 |
| 2 | 2-Chlorophenyl 2-fluoroethyl ether | |
| 3 | 2-Bromophenyl 2-fluoroethyl ether | |
| 4 | 2-Fluoroethyl 2-iodophenyl ether | |
| 5 | 2-Fluoroethyl 2-methylphenyl ether | |
| 6 | 2-Fluoroethyl 2-(1-methylethyl)phenyl ether | 59/0.2 |
| 7 | 2-Fluoroethyl 2-(1,1-dimethylethyl)phenyl ether | 70/0.2 |
| 8 | 2-Fluoroethyl 2-hydroxymethylphenyl ether | 110/0.2 |
| 9 | 2-Cyanophenyl 2-fluoroethyl ether | |
| 10 | 2-Fluoroethyl ([1,1'-biphenyl]-2-yl) ether | |
| 11 | 2-Fluoroethoxybenzaldehyde | |
| 12 | 2-Fluoroethyl 2-(1-oxopropyl)phenyl ether | 51–52 |
| 13 | Methyl 2-(2-fluoroethoxy)benzoate | |
| 14 | Ethyl 2-(2-fluoroethoxy)benzoate | |
| 15 | 2-Aminophenyl 2-fluoroethyl ether | |
| 16 | 2-Ethylaminophenyl 2-fluoroethyl ether | |
| 18 | 2-Fluoroethyl 2-nitrophenyl ether | |
| 19 | 2-Fluoroethyl 2-methoxyphenyl | |
| 20 | 2-Fluoroethyl 2-difluoromethoxyphenyl ether | |
| 21 | 2-Fluoroethyl 2-methylthiophenyl ether | |
| 22 | 2-Fluoroethyl 2-methylsulfinylphenyl ether | |
| 23 | 2-Fluoroethyl 2-methyl sulfonylphenyl ether | 67–69 |

TABLE 1-continued

| Cmpd No. | Name | M.P. (°C.) B.P. (°C./mm) |
|---|---|---|
| 24 | 2-Fluoroethyl 3-fluorophenyl ether | |
| 25 | 3-Chlorophenyl 2-fluoroethyl ether | |
| 26 | 3-Bromophenyl 2-fluoroethyl ether | |
| 27 | 2-Fluoroethyl 3-iodophenyl ether | |
| 28 | 2-Fluoroethyl 3-methylphenyl ether | |
| 29 | 3-Ethylphenyl 2-fluoroethyl ether | |
| 30 | 2-Fluoroethyl 3-(1-methylethyl)phenyl ether | |
| 31 | 2-Fluoroethyl 3-(1,1-dimethylethyl)phenyl ether | |
| 32 | 2-Fluoroethyl 3-trifluoromethylphenyl ether | |
| 33 | 3-Cyanophenyl 2-fluoroethyl ether | |
| 34 | 3-(2-Fluoroethoxy)benzaldehyde | |
| 35 | 3-Acetylphenyl 2-fluoroethyl ether | |
| 37 | Methyl 3-(2-fluoroethoxy)benzoate | |
| 38 | Ethyl 3-(2-fluoroethoxy)benzoate | |
| 39 | 3-Aminophenyl 2-fluoroethyl ether | |
| 40 | 3-Ethylaminophenyl 2-fluoroethyl ether | |
| 41 | 2-Fluoroethyl 3-dimethylaminophenyl ether | |
| 43 | 2-Fluoroethyl 3-nitrophenyl ether | |
| 44 | 2-Fluoroethyl 3-hydroxyphenyl ether | |
| 45 | 2-Fluoroethyl 3-methoxyphenyl ether | |
| 46 | 2-Fluoroethyl 3-difluoromethoxyphenyl ether | |
| 47 | 2-Fluoroethyl 3-phenoxyphenyl ether | |
| 48 | 2-Fluoroethyl 3-(thien-2-yl)phenyl ether | |
| 49 | 4-Bromophenyl 2-fluoroethyl ether | |
| 50 | 2-Fluoroethyl 4-iodophenyl ether | 49–50 |
| 51 | 2-Fluoroethyl 4-methylphenyl ether | |
| 52 | 2-Fluoroethyl 4-(1-methylethyl)phenyl ether | |
| 53 | 2-Fluoroethyl 4-(1,1-dimethylethyl)phenyl ether | |
| 54 | 2-Fluoroethyl 4-trifluoromethylphenyl ether | |
| 55 | 2-Fluoroethyl 4-hydroxymethyl phenyl ether | |
| 56 | 4-Cyanophenyl 2-fluoroethyl ether | |
| 57 | 2-Fluoroethyl ([1,1'-biphenyl]-4-yl) ether | |
| 58 | 4,4'-di(2-Fluoroethoxy)-[1,1'-phenyl] | |
| 59 | 4-(2-Fluoroethoxymethyl)phenyl 2-fluoroethyl ether | |
| 60 | 4-(2-Fluoroethoxy)benzaldehyde | 54–55 |
| 61 | 4-Acetylphenyl 2-fluoroethyl ether | 50.5–52 |
| 62 | 4-Ethylcarbonylphenyl 2-fluoroethyl ether | 83–84 |
| 64 | 2-Fluoroethyl 4-[4-(2-fluoroethoxy)benzoyl]phenyl ether | |
| 65 | Methyl 4-(2-fluoroethoxy)benzoate | |
| 66 | Ethyl 4-(2-fluoroethoxy)benzoate | |
| 67 | 4-aminophenyl 2-fluoroethyl | 44–45 |

TABLE 1-continued

| Cmpd No. | Name | M.P. (°C.) B.P. (°C./mm) |
|---|---|---|
| | ether | |
| 69 | 4-Ethylaminophenyl 2-fluoroethyl ether | |
| 71 | 2-Fluoroethyl 4-nitrophenyl ether | |
| 72 | N-[4-(2-Fluoroethoxy)phenyl]-benzenemethanimine | |
| 73 | 2-Fluoroethyl 4-hydroxyphenyl ether | |
| 74 | 2-Fluoroethyl 4-methoxyphenyl ether | |
| 75 | 2-Fluoroethyl 4-pentoxyphenyl ether | |
| 76 | 2-Fluoroethyl 4-difluoromethoxyphenyl ether | |
| 77 | 2-Fluoroethyl 4-phenoxyphenyl ether | |
| 78 | 2-Fluoroethyl 4-mercaptophenyl ether | |
| 79 | 2-Fluoroethyl 4-methylthiophenyl ether | |
| 80 | 2-Fluoroethyl 4-methylsulfinylphenyl ether | |
| 81 | 2-Fluoroethyl 4-methylsulfonylphenyl ether | |
| 82 | 2-Fluoroethyl 2,4-difluorophenyl ether | 95/20 |
| 83 | 2-Fluoroethyl 2,6-difluorophenyl ether | 95/25 |
| 84 | 4-Bromo-2-chlorophenyl 2-fluoroethyl ether | 50–51 |
| 85 | 4-Chloro-3-methylphenyl 2-fluoroethyl ether | |
| 86 | 2-Bromo-4-methylphenyl 2-fluoroethyl ether | |
| 87 | 4-Cyano-2-nitrophenyl 2-fluoroethyl ether | |
| 88 | 2-Cyano-4-nitrophenyl 2-fluoroethyl ether | |
| 89 | 2-Fluoroethyl 2,3-dimethylphenyl ether | |
| 90 | 2-Fluoroethyl 5-methyl-2-nitrophenyl ether | 57–58 |
| 91 | 2-Fluoroethyl 3-methyl-4-nitrophenyl ether | 55–56 |
| 92 | 2-Fluoroethyl 2,4-dinitrophenyl ether | |
| 93 | 2-Fluoroethyl pentafluorophenyl ether | |
| 94 | 7-(2-Fluoroethoxy)-2,3-dihydro-2,2-dimethylbenzofuran | |
| 95 | 1,2-Di(2-fluoroethoxy)benzene | |
| 96 | 2,3-Di(2-fluoroethoxy)toluene | |
| 97 | 1,2-Di(2-fluoroethoxy)-3-(1-methylethyl)benzene | |
| 98 | 3-Bromomethyl-1,2-di(2-fluoroethoxy)benzene | 99–100 |
| 99 | 3-Cyano-1,2-di(2-fluoroethoxy)-benzene | 53–54 |
| 100 | 3-(3-Oxobutyl)-1,2-di(2-fluoroethoxy)benzene | |
| 101 | 3-[2,3-Di(2-fluoroethoxy)-phenyl]propanoic acid | 109–110 |
| 102 | 2,3-Di(2-fluoroethoxy)benzaldehyde | |
| 103 | 2,3-Di(2-fluoroethoxy)benzamide | 100–101 |
| 104 | 2,3-Di(2-fluoroethoxy)-N-methylbenzamide | 117–118 |
| 105 | 2,3-Di(2-fluoroethoxy)benzoic acid | 104–105 |
| 106 | Methyl 2,3-di(2-fluoroethoxy)-benzoate | |
| 107 | Ethyl 2,3-di(2-fluoroethoxy)-benzoate | |
| 108 | 2-Fluoroethyl 2,3-di(2-fluoroethoxy)benzoate | 47–48.5 |
| 109 | 1,2-Di(2-fluoroethoxy)-3-methoxybenzene | |
| 110 | 4-Bromo-1,2-di(2-fluoroethoxy)benzene | 57–60 |

TABLE 1-continued

| Cmpd No. | Name | M.P. (°C.) B.P. (°C./mm) |
|---|---|---|
| 111 | 3,4-Di(2-fluoroethoxy)toluene | |
| 112 | 1,2-Di(2-fluoroethoxy)-4-(1,1-dimethylethyl)benzene | |
| 113 | 4-Cyano-1,2-di(2-fluoroethoxy)-benzene | |
| 114 | 3,4-Di(2-fluoroethoxy)benzaldehyde | |
| 115 | 2-Fluoroethyl 3,4-di(2-fluoroethoxy)benzoate | |
| 116 | 1,2-Di(2-fluoroethoxy)-4-nitrobenzene | |
| 117 | 2-Fluoroethyl 3,4-di(2-fluoroethoxy)-5-nitrobenzoate | |
| 118 | 1,3-Di(2-fluoroethoxy)benzene | |
| 119 | 2-Acetyl-1,3-di(2-fluoroethoxy)-benzene | |
| 120 | 2,6-Di(2-fluoroethoxy)benzoic acid | 57–58.5 |
| 121 | 2-Fluoroethyl 2,6-di(2-fluoroethoxy)benzoate | 60–60.5 |
| 122 | 2,6-di(2-fluoroethoxy)aniline | |
| 123 | 4-Bromo-1,3-di(2-fluoroethoxy)-benzene | 65–67 |
| 124 | 2,4-di(2-fluoroethoxy)toluene | 83–85 |
| 125 | 4-Cyano-1,3-di(2-fluoroethoxy)-benzene | |
| 126 | 2,4-di(2-fluoroethoxy)benzaldehyde | |
| 127 | 4-Acetyl-1,3-di(2-fluoroethoxy)-benzene | |
| 128 | 1,3-Di(2-fluoroethoxy)-4-(1-oxohexyl)benzene | |
| 129 | 2,4-Di(2-fluoroethoxy)benzamide | 136–139 |
| 130 | 2,4-Di(2-fluoroethoxy)benzoic acid | 138–139 |
| 131 | 2-Fluoroethyl 2,4-di(2-fluoroethoxy)benzoate | 63–64 |
| 132 | 3,5-Di(2-fluoroethoxy)toluene | |
| 133 | 1,3-Di(2-fluoroethoxy)-5-pentylbenzene | |
| 134 | 5-Cyano-1,3-di(2-fluoroethoxy)-benzene | |
| 135 | 1,3-Di(2-fluoroethoxy)-5-methoxybenzene | |
| 136 | 3,5-Di(2-fluoroethoxy)benzamide | 104–105 |
| 137 | 1,4-Di(2-fluoroethoxy)benzene | 87–89 |
| 138 | 2-Bromo-1,4-di(2-fluoroethoxy)-benzene | |
| 139 | 1,4-Di(2-fluoroethoxy)-2-(1,1-dimethylethyl)benzene | |
| 140 | 2-Cyano-1,4-di(2-fluoroethoxy)-benzene | |
| 141 | 2,5-di(2-fluoroethoxy)benzaldehyde | |
| 142 | 2-Acetyl-1,4-di(2-fluoroethoxy)-benzene | |
| 143 | 2,5-Di(2-fluoroethoxy)benzoic acid | 93–94 |
| 146 | 1,2,3-Tri(2-fluoroethoxy)benzene | |
| 147 | 4-Cyano-1,2,3-tri(2-fluoroethoxy)benzene | 102–104 |
| 148 | 2,3,4-Tri(2-fluoroethoxy)benzaldehyde | 68–70.5 |
| 149 | 4-Acetyl-1,2,3-tri(2-fluoroethoxy)benzene | |
| 150 | 3-[2,3,4-Tri(2-fluoroethoxy)-phenyl]propanoic acid | |
| 151 | 1,3,5-Tri(2-fluoroethoxy)benzene | |
| 152 | 2-Cyano-1,3,5-tri(2-fluoroethoxy)benzene | |
| 153 | 2,4,6-Tri(2-fluoroethoxy)-benzaldehyde | |
| 154 | 1-Cyano-2-(2-fluoroethoxy)-naphthalene | |
| 155 | 2-(2-Fluoroethoxy)-1-hydroxymethylnaphthalene | |
| 156 | 2-(2-fluoroethoxy)-1-naphthaldehyde | |
| 157 | 6-Bromo-2-(2-fluoroethoxy)-naphthalene | |

TABLE 1-continued

| Cmpd No. | Name | M.P. (°C.) B.P. (°C./mm) |
|---|---|---|
| 158 | 2-(2-Fluoroethoxy)-6-(1-methylethyl)naphthalene | 46–48 |
| 160 | 2-(2-fluoroethoxy)-6-naphthaldehyde | 51–54 |
| 162 | 1,3-Di(2-fluoroethoxy)naphthalene | |
| 163 | 1,4-Di(2-fluoroethoxy)naphthalene | |
| 164 | 1,5-Di(2-fluoroethoxy)naphthalene | |
| 165 | 1,6-Di(2-fluoroethoxy)naphthalene | |
| 166 | 1,7-Di(2-fluoroethoxy)naphthalene | |
| 167 | 2,3-Di(2-fluoroethoxy)naphthalene | |
| 168 | 2,6-Di(2-fluoroethoxy)naphthalene | |
| 169 | 2,7-Di(2-fluoroethoxy)naphthalene | |
| 177 | 2-Fluoroethyl benzyl ether | |
| 178 | 2-Fluorobenzyl 2-fluoroethyl ether | |
| 179 | 2-Chlorobenzyl 2-fluoroethyl ether | |
| 180 | 2-Bromobenzyl 2-fluoroethyl ether | |
| 181 | 2-Fluoroethyl 2-methylbenzyl ether | |
| 182 | 2-Fluoroethyl 2-trifluoromethylbenzyl ether | |
| 183 | 2-Cyanobenzyl 2-fluoroethyl ether | |
| 184 | 2-Fluoroethyl 2-methoxybenzyl ether | |
| 185 | 3-Fluorobenzyl 2-fluoroethyl ether | |
| 186 | 3-Chlorobenzyl 2-fluoroethyl ether | |
| 187 | 3-Bromobenzyl 2-fluoroethyl ether | |
| 188 | 2-Fluoroethyl 3-methylbenzyl ether | |
| 189 | 3-Cyanobenzyl 2-fluoroethyl ether | |
| 190 | 2-Fluoroethyl 3-nitrobenzyl ether | |
| 191 | 2-Fluoroethyl 3-methoxybenzyl ether | |
| 192 | 4-Fluorobenzyl 2-fluoroethyl ether | |
| 193 | 4-Chlorobenzyl 2-fluoroethyl ether | |
| 194 | 4-Bromobenzyl 2-fluoroethyl ether | |
| 195 | 2-Fluoroethyl 4-methylbenzyl ether | |
| 196 | 2-Fluoroethyl 4-(1-methylethyl)benzyl ether | |
| 197 | 2-Fluoroethyl 4-trifluoromethylbenzyl ether | |
| 198 | 4-Cyanobenzyl 2-fluoroethyl ether | |
| 199 | 2-Fluoroethyl 4-methoxybenzyl ether | |
| 200 | 2-Fluoroethyl 4-methylthiobenzyl ether | |
| 201 | 2-Fluoroethyl 4-methylsulfonylbenzyl ether | |
| 202 | 2,6-Dichlorobenzyl 2-fluoroethyl ether | |
| 203 | 2-Fluoroethyl 2-methyl-3-nitrobenzyl ether | |
| 204 | 1,2-Di(2-fluoroethoxymethyl)benzene | |
| 205 | 2-Fluoroethyl pentafluorobenzyl ether | |
| 206 | 2-Fluoroethyl diphenylmethyl ether | |
| 207 | 1-(2-Chlorophenyl)ethyl 2-fluoroethyl ether | |
| 208 | 1-(2-Chlorophenyl)-2-methylpropyl 2-fluoroethyl ether | |
| 209 | 2-Chloro-α-phenylbenzyl 2-fluoroethyl ether | |
| 210 | 3,4-Dichlorobenzyl 2-fluoroethyl ether | |
| 211 | 3,5-Dichlorobenzyl 2-fluoroethyl ether | |
| 212 | 2,3,5-Trichlorobenzyl 2-fluoroethyl ether | |
| 213 | 2,3,5,6-Tetrafluoro-4-methylbenzyl 2-fluoroethyl ether | 118–121 |
| 214 | 1-(2-fluoroethoxy)naphthalene | |
| 215 | 4-Chloro-1-(2-fluoroethoxy)naphthalene | |
| 216 | 4-Bromo-1-(2-fluoroethoxy)naphthalene | |
| 217 | 1-(2-Fluoroethoxy)-4-iodonaphthalene | 50 |
| 218 | 1-(2-Fluoroethoxy)-4-methylnaphthalene | |
| 219 | 1-(2-Fluoroethoxy)-4-(1-methylethyl)naphthalene | |
| 220 | 1-(2-Fluoroethoxy)-4-cyclopentylnaphthalene | |
| 221 | 1-(2-Fluoroethoxy)-4-(2-fluoroethoxymethyl)naphthalene | |
| 222 | 1-(2-Fluoroethoxy)-4-methoxynaphthalene | 95–97 |
| 223 | 1-(2-Fluoroethoxy)-4-(1-methylethoxy)naphthalene | |
| 224 | 4-Cyano-1-(2-fluoroethoxy)naphthalene | |
| 225 | 4-(2-Fluoroethoxy)naphthaldehyde | 81 |
| 226 | 1-(2-Fluoroethoxy)-4-nitronaphthalene | |
| 227 | 1-(2-Fluoroethoxy)-4-phenylnaphthalene | |
| 228 | 1-(2-Fluoroethoxymethyl)naphthalene | |
| 229 | 4-Fluoro-1-(2-fluoroethoxymethyl)naphthalene | |
| 230 | 1-(2-Fluoroethoxymethyl)-4-methoxynaphthalene | |
| 231 | 1-(2-Fluoroethoxymethyl)-4-(N,N-dimethylamino)naphthalene | |

While many of these compounds are the same as or very similar to compounds known in the art, their insecticidal/nematicidal properties have not been reported. Certain of them, however, are themselves new chemical entities which have not been reported in the literature. The novel compounds have the general formula $R^1R^2mAr(OCH_2CH_2F)_n$ in which:

Ar is phenyl and n is 1 to 3, or Ar is naphthyl and n is 1 or 2, or Ar is phenylmethyl, (alkyl)(phenyl)methyl, diphenylmethyl, or naphthylmethyl and n is 1; and m is 0 and $R^1$ is selected from lower alkylcarbonyl(lower)alkyl, carboxyalkyl, halomethyl, fluoroethoxymethyl, cyano, carboxyl, alkylcarbonyl, alkylaminocarbonyl, aminocarbonyl, fluoroethoxycarbonyl, fluoroethoxyphenylcarbonyl, alkylamino, dialkylamino, alkylcarbonylamino, phenylmethanimido, alkoxy, difluoromethoxy, mercapto, methylthio, methylsulfinyl, methylsulfonyl, phenoxy, phenyl, fluoroethoxyphenyl, thienyl, or a group of the formula —OC(CH₃)₂CH₂— bridging adjacent carbon atoms of a phenyl ring, with the proviso that Ar is other than naphthyl when $R^1$ is carboxyl, alkoxycarbonyl, aminocarbonyl, methylthio, or hydroxy; or m is 1, $R^1$ is selected from alkyl, halogen, cyano, nitro and fluoroethoxycarbonyl, and $R^2$ is selected from alkyl, halogen and nitro; or m is 2–5, and $R^1$ methyl or halogen and $R^2$ is halogen.

INSECTICIDAL AND ACARICIDAL TESTS

The compounds were tested for insecticidal activity according to the procedures summarized below.

Foliar screening and evaluations were conducted against Mexican bean beetle (*Epilachna varivestis*), pea aphid (*Acyrthosiohon pisum*), southern armyworm (*Spodoptera eridania*), cabbage looper (*Trichoplusia ni*), and twospotted spider mite (*Tetranychus urticae*). In general, the test compounds were applied to whole plants by spraying to runoff with a 10% acetone-0.25% octylphenoxypolyethanol-water solution containing from 0.5 to 1000 ppm of the test compound. Two replicates for each rate of application were used. Specific test procedures are outlined below.

Leaves infested with adult twospotted spider mites were removed from culture plants and cut into segments containing 50–75 female mites. Each segment was placed onto the upper leaf surface of a whole pinto bean (*Phaseolus vulgaris*) plant. After the mites had migrated to the under surfaces of the leaves, the leaf segments used to infest were removed and each plant sprayed with test chemical as described above. After the plants dried, the entire plant and pot were placed in metal trays. A supply of water in the tray kept the plants turgid throughout the 48 hour exposure period.

In tests utilizing pea aphid whole fava bean (*Vicia faba*) plants were sprayed with test chemical and allowed to dry as described above. Individual test plants in their pots were placed in 48 ounce waxed containers. Ten adult pea aphids, selected for uniformity of size and vigor were counted into each container. Each container was covered with a glass petri dish and placed on a rack where it was held for 48 hours as described above.

In foliar tests utilizing the Mexican bean beetle, the southern armyworm, or the cabbage looper, the pinto bean test plants were sprayed with test chemical and allowed to dry as previously described. Each test plant was cut off at the soil line and the stem was pushed through a small diameter hole punched in the bottom of an eight ounce waxed container. Ten first instar Mexican bean beetle, cabbage looper, or southern armyworm larvae were counted into each container. Each container was covered with a glass petri dish and, with the plant stem protruding from the bottom, placed on a holding rack which allowed the stem to remain in water throughout the 24 or 48 hour exposure period.

A Contact Assay was conducted to evaluate the test compound against first instar cabbage loopers. Aloquots (100 μl) of test solutions containing various amounts of the candidate insecticide dissolved in acetone was placed into a glass vial. The vial was twirled by hand to coat the entire interior of each vial, and then placed in an exhaust hood for one hour to evaporate the acetone. The treated vials were infested with five first instar cabbage loopers and the vial was capped. After 24 hours the percent mortality was determined.

Insecticidal and acaricidal data were collected and recorded at the end of the 24 or 48 hour exposure period. In the case of Mexican bean beetle, cabbage looper, pea aphid, and southern armyworm, the containers were opened and the numbers of dead and live insects were counted. Moribund larvae, which were disoriented or unable to crawl normally, were counted as dead. Twospotted spider mites were counted with the aid of a binocular microscope at approximately 10× magnification. Each leaf was detached from the plant and placed on the microscope stage. Only live adult female mites on the underside of the leaf were counted. Moribund mites were considered dead.

Total test organisms and number dead were recorded for each replicate. These data were used to generate percent mortality values.

The results of the foliar and contact tests are reported in Table II. A "+" indicates the test compound exhibited at least 20% mortality at a test rate in the range of 25 to 1000 ppm for foliar tests, 25 to 1000 μg/insect in the contact test; A "−" indicates marginal or no control. Where more than one type of test was run with different results, both results are summarized as described above, separated by a slash.

The compounds were also subjected to a soil incorporated southern corn rootworm test to evaluate the soil insecticidal activity of the candidate insecticide at rates of 64.0 to 0.25 ppm in soil containing corn sprouts and southern corn rootworm larvae. Five milliliters of a 10% acetone/water solution containing the appropriate amount of candidate insecticide was pipetted into 50 grams of air-dried soil in a 3 ounce plastic cup. The treated soil was allowed to stand uncovered in a hood for 30 minutes to evaporate the acetone. The process was duplicated for each rate of application. The dried, treated soil in each cup was thoroughly mixed and two 3-day-old corn sprouts and ten early third stage (9–10 days old) southern corn rootworm larvae were placed in each cup. The cups were covered with a plastic lid, placed in a closed plastic bag, and incubated in a holding room at 23°–26° C. for 2 days. After this time, the unaffected larvae were extracted from the soil and percent mortality determined.

Table II summarizes the initial activity of the present compounds under the column headed "SCR". Those compounds showing a kill rate of at least 20 percent in the initial test are indicated by a "+", those exhibiting less than 20 percent control by "−".

Systemic Test Procedure

A number of the compounds disclosed herein have exhibited good to excellent upward systemic insecticidal activity. Systemic assays were conducted by first placing the bottom or lid of a 100×15 mm plastic petri dish under each potted test plant to contain the toxicant. The soil of each test plant is drenched with 25 mL of the test solution containing the appropriate amount of the candidate insecticide. Care was taken not to wet foliage or stem of the plant with the test solution. After treatment, the plants are moved to a greenhouse for a three day translocation period. The test plants are then infested and held. Data is taken in the same manner as described in the foliar tests. Table 5 summarizes the systemic activity against beet armyworm, pea aphids, southern armyworm and twospotted spider mite.

The results of this test are also summarized in Table II under the heading "Systemic Activity". A "+" indicates at least 20% control of one of the test species at a rate in the range of 25–200 ppm, a "−" indicating less than 20 percent control.

TABLE II

| Cmpd. Nos. | PA | CL | MBB | SAW | TSM | SCR | Systemic Activity | C. Elegans (5 ppm) | Rootknot (10 ppm) |
|---|---|---|---|---|---|---|---|---|---|
| 1 | − | + | − | − | − | − |   |   | − |
| 2 | + | + | − | − | − | − |   | − | + |
| 3 | + | − | − | − | − | − | + | − | + |
| 4 | + | + | − | − | − | + | + |   |   |
| 5 | + | + | − | − | − | − | + | − | + |
| 6 | + | −/+ | − | − | − | + | + | − | − |
| 7 | − | − | − | − | − | − | + | − | − |
| 8 | + | − | − | − | − | − | − | − | − |
| 9 | + | + | − | − | − | − | − | − | + |

TABLE II-continued

| Cmpd. Nos. | PA | CL | MBB | SAW | TSM | SCR | Systemic Activity | C. Elegans (5 ppm) | Rootknot (10 ppm) |
|---|---|---|---|---|---|---|---|---|---|
| 10 | − | + | − | − | − | − | − | | − |
| 11 | + | −/+ | − | − | − | − | − | − | + |
| 12 | + | + | − | − | − | + | − | | |
| 13 | − | + | − | − | − | − | − | − | − |
| 14 | − | + | − | − | − | − | − | − | |
| 15 | − | + | − | − | − | − | − | | − |
| 16 | − | −/+ | − | − | − | − | − | − | − |
| 18 | + | + | − | − | −/+ | − | + | | + |
| 19 | + | − | − | − | − | − | + | − | − |
| 20 | + | −/+ | − | − | − | + | + | − | + |
| 21 | + | + | − | − | − | − | + | | − |
| 22 | + | + | − | − | + | − | − | | − |
| 23 | + | + | − | − | − | − | − | | − |
| 24 | + | − | − | − | − | − | + | − | − |
| 25 | + | −/+ | − | − | − | − | + | − | − |
| 26 | + | + | − | − | − | − | + | − | + |
| 27 | + | + | − | − | − | − | + | | |
| 28 | + | − | − | − | − | − | − | − | − |
| 29 | + | −/+ | − | − | − | − | + | | + |
| 30 | + | −/+ | − | − | − | − | + | − | + |
| 31 | + | −/+ | − | − | − | + | + | − | + |
| 32 | + | −/+ | − | − | − | − | + | − | − |
| 33 | + | + | − | − | − | − | + | − | + |
| 34 | − | + | − | − | − | − | − | − | − |
| 35 | + | + | − | − | − | − | + | − | − |
| 37 | − | + | − | − | − | − | − | − | − |
| 38 | − | + | − | − | − | − | − | | − |
| 39 | +/− | + | − | − | − | − | − | − | − |
| 40 | − | + | − | − | − | + | − | − | − |
| 41 | + | + | − | − | − | − | + | − | + |
| 43 | − | + | − | − | − | − | − | | − |
| 44 | − | + | − | − | − | − | − | − | + |
| 45 | + | + | − | − | − | − | + | − | + |
| 46 | + | − | − | − | − | + | + | | |
| 47 | + | + | − | − | − | − | − | − | + |
| 48 | − | + | − | − | − | − | − | + | + |
| 49 | + | + | − | − | − | − | + | − | + |
| 50 | + | + | − | − | − | − | + | | |
| 51 | + | − | − | − | − | − | + | − | − |
| 52 | − | −/+ | − | − | − | + | − | − | + |
| 53 | − | − | − | − | − | − | − | − | + |
| 54 | + | −/+ | − | − | − | − | + | − | + |
| 55 | − | + | − | − | − | − | − | − | − |
| 56 | + | + | − | −/+ | − | − | + | − | + |
| 57 | − | + | − | − | − | − | − | + | + |
| 58 | − | + | − | − | − | − | − | + | + |
| 59 | + | + | − | − | − | − | + | − | + |
| 60 | + | + | − | − | − | − | + | − | +/− |
| 61 | + | − | − | − | −/+ | − | + | − | |
| 62 | + | + | − | − | − | − | + | − | − |
| 64 | − | + | − | − | − | − | − | − | + |
| 65 | + | − | − | − | − | − | − | − | − |
| 66 | + | + | − | − | − | − | − | − | + |
| 67 | − | + | − | − | − | − | − | − | − |
| 69 | + | + | − | − | − | − | + | − | + |
| 71 | + | + | − | −/+ | − | − | − | | + |
| 72 | + | + | − | − | − | − | + | − | − |
| 73 | − | + | − | − | − | − | − | − | − |
| 74 | + | + | − | − | − | − | + | − | + |
| 75 | − | − | + | − | + | − | − | + | − |
| 76 | + | + | − | − | − | + | + | − | + |
| 77 | + | + | − | − | − | − | − | + | + |
| 78 | +/− | + | − | − | − | − | − | + | − |
| 79 | + | + | − | + | + | − | + | − | + |
| 80 | + | + | − | − | − | − | + | − | − |
| 81 | + | + | − | −/+ | − | − | − | − | + |
| 82 | + | − | − | − | − | − | + | | |
| 83 | − | − | − | − | − | − | − | | |
| 84 | + | | − | − | − | − | − | | − |
| 85 | − | | − | − | − | + | + | | + |
| 86 | + | | − | − | − | − | − | − | + |
| 87 | − | + | − | − | − | − | − | − | +/− |
| 88 | +/− | + | − | − | − | − | − | − | − |
| 89 | − | | − | − | − | − | − | − | + |
| 90 | − | + | − | − | − | − | − | − | − |
| 91 | + | + | − | −/+ | − | − | + | − | + |
| 92 | − | + | − | − | − | − | − | − | +/− |
| 93 | +/− | − | − | − | − | − | + | − | − |
| 94 | − | | − | − | − | − | + | | − |
| 95 | − | | − | − | − | − | − | − | + |

TABLE II-continued

| Cmpd. Nos. | PA | CL | MBB | SAW | TSM | SCR | Systemic Activity | C. Elegans (5 ppm) | Rootknot (10 ppm) |
|---|---|---|---|---|---|---|---|---|---|
| 96 | +/− | + | − | − | − | − | + | − | − |
| 97 | + | − | − | − | − | − | + | − | + |
| 98 | + | − | − | − | − | − | − | − | − |
| 99 | + | + | − | − | − | − | − | − | + |
| 100 | − | + | − | − | − | − | − | − | − |
| 101 | + | + | − | − | − | − | − | − | − |
| 102 | −/+ | − | − | − | − | − | − | − | − |
| 103 | + | + | − | − | − | − | + | − | + |
| 104 | + | + | − | − | − | − | − | − | + |
| 105 | −/+ | + | − | − | − | − | − | − | − |
| 106 | + | + | − | − | − | − | − | − | + |
| 107 | + | + | − | − | − | − | − | − | + |
| 108 | + | + | − | − | − | − | − | − | − |
| 109 | + | + | − | −/+ | − | − | − | − | − |
| 110 | + | − | − | − | − | + | + | − | − |
| 111 | + | − | − | − | − | − | + | − | − |
| 112 | − | − | − | + | − | + | − | − | − |
| 113 | + | + | − | − | − | − | + | − | + |
| 114 | − | − | − | − | − | − | − | − | − |
| 115 | + | − | − | − | + | − | − | − | − |
| 116 | − | + | − | − | − | − | − | − | + |
| 117 | − | + | − | − | − | − | − | − | − |
| 118 | + | + | − | − | − | − | + | − | + |
| 119 | + | + | − | − | − | − | − | − | + |
| 120 | + | + | − | − | − | − | − | | |
| 121 | + | + | − | − | − | + | − | | |
| 122 | + | + | − | − | + | + | − | | |
| 123 | + | + | − | − | − | +/− | − | | |
| 124 | + | + | − | − | − | + | + | | |
| 125 | + | + | − | − | − | + | + | − | + |
| 126 | − | − | − | − | − | − | − | − | − |
| 127 | + | + | − | − | − | − | − | | |
| 128 | − | + | − | − | + | − | − | + | − |
| 129 | + | + | − | − | − | + | + | | |
| 130 | +/− | + | − | − | − | + | − | | |
| 131 | − | + | − | − | − | − | − | | |
| 132 | + | + | − | − | − | − | − | | + |
| 133 | − | + | − | − | − | − | − | | |
| 134 | − | + | − | − | − | − | − | − | + |
| 135 | + | + | − | − | − | − | − | − | − |
| 136 | − | − | + | − | − | + | − | | |
| 137 | + | + | − | − | − | − | + | − | + |
| 138 | + | + | − | + | + | + | + | | |
| 139 | + | + | − | − | + | + | + | | |
| 140 | + | + | − | − | + | − | − | − | + |
| 141 | − | − | − | − | − | − | − | − | − |
| 142 | + | + | − | − | − | − | + | − | + |
| 143 | + | − | − | − | − | −/+ | − | | |
| 146 | + | + | − | − | − | − | − | | |
| 147 | + | + | − | −/+ | − | − | − | − | − |
| 148 | − | + | − | − | − | + | − | − | − |
| 149 | + | + | − | − | − | − | − | − | − |
| 150 | − | − | − | − | − | − | − | − | − |
| 151 | +/− | + | − | − | − | − | − | − | + |
| 152 | − | + | − | − | − | − | − | − | − |
| 153 | − | + | − | − | − | − | − | − | − |
| 154 | − | − | − | − | − | − | − | − | + |
| 155 | − | −/+ | − | − | − | + | − | − | + |
| 156 | − | + | − | − | − | + | − | − | − |
| 157 | − | + | − | − | − | + | + | + | + |
| 158 | + | − | − | − | − | + | − | | |
| 159 | + | −/+ | − | − | − | − | + | − | + |
| 160 | + | + | − | − | − | − | + | − | + |
| 163 | + | + | − | − | − | − | + | + | + |
| 164 | − | + | − | − | − | − | + | − | + |
| 165 | + | + | − | − | − | + | + | + | + |
| 166 | − | − | − | − | − | − | − | − | + |
| 167 | + | − | − | − | − | − | + | − | − |
| 168 | + | + | − | − | − | − | + | − | + |
| 169 | + | + | − | − | − | − | + | + | + |
| 177 | + | −/+ | − | − | − | − | + | − | + |
| 178 | − | − | − | − | − | − | − | | + |
| 179 | − | − | − | + | − | + | − | | |
| 180 | + | − | − | − | − | + | + | − | + |
| 181 | + | − | − | − | − | + | + | | + |
| 182 | + | + | − | − | − | + | + | | − |
| 183 | + | + | − | − | − | + | + | − | + |
| 184 | − | + | − | − | − | − | − | − | − |
| 185 | + | + | − | − | − | + | + | − | + |
| 186 | + | + | − | − | − | + | + | | + |

TABLE II-continued

| Cmpd. Nos. | PA | CL | MBB | SAW | TSM | SCR | Systemic Activity | C. Elegans (5 ppm) | Rootknot (10 ppm) |
|---|---|---|---|---|---|---|---|---|---|
| 187 | + | + | − | − | − | + | + | | |
| 188 | + | −/+ | − | − | − | − | + | | + |
| 189 | + | + | − | −/+ | + | − | + | | + |
| 190 | + | + | − | −/+ | + | − | − | | + |
| 191 | + | + | − | − | − | − | + | − | + |
| 192 | − | − | − | − | − | + | + | − | + |
| 193 | + | + | − | − | − | + | + | | + |
| 194 | + | + | + | − | − | + | + | − | + |
| 195 | + | − | − | − | − | − | + | | + |
| 196 | + | + | − | − | − | + | − | − | + |
| 197 | + | −/+ | − | − | − | + | + | | |
| 198 | + | + | − | − | − | − | + | | |
| 199 | − | + | − | − | − | + | − | − | + |
| 200 | − | + | + | − | + | + | + | | |
| 201 | + | + | − | + | − | − | + | | |
| 202 | + | + | − | − | − | − | + | | − |
| 203 | + | + | − | + | + | + | + | − | + |
| 204 | + | − | − | − | − | − | + | − | + |
| 205 | + | + | − | − | − | + | − | | + |
| 206 | + | + | − | − | − | + | − | | − |
| 207 | + | − | − | − | − | + | + | | |
| 208 | + | − | − | − | − | + | + | | |
| 209 | + | − | − | − | − | − | + | | |
| 210 | − | + | − | − | + | − | + | | |
| 211 | + | − | − | − | + | + | + | | |
| 212 | + | + | − | − | + | − | + | | |
| 213 | − | − | − | − | − | + | − | | |
| 214 | + | + | − | − | + | − | + | | |
| 215 | + | − | − | − | + | − | − | | |
| 216 | − | − | − | − | − | − | − | | |
| 217 | + | − | − | − | + | − | − | | |
| 218 | + | − | − | − | + | − | − | | |
| 219 | + | − | − | − | + | − | − | | |
| 220 | + | − | − | − | + | − | − | | |
| 221 | + | + | + | − | − | − | + | | |
| 222 | + | − | − | − | + | − | − | | |
| 223 | + | − | − | − | + | − | − | | |
| 224 | + | − | − | − | + | − | − | | |
| 225 | + | − | − | − | + | − | − | | |
| 226 | + | + | − | − | + | − | − | | |
| 227 | + | − | − | − | + | − | − | | |
| 228 | − | − | − | − | + | − | + | | |
| 229 | + | + | − | − | + | − | − | | |
| 230 | − | − | − | − | − | − | + | | |
| 231 | + | − | − | − | + | − | − | | |

NEMATICIDE TESTS

Nematicide activity has also been exhibited by the present compounds when tested against the soil-borne root-knot nematode (*Meloidogyne incognita*), the stunt nematode (*Tylenchorhynchus claytoni*), the lesion nematode (*Pratylenchus penetrans*), the soybean cyst nematode (*Heterodera glycines*), and the free-living *Caenorhabditis elegans*.

Activity against the free-living nematode, *Caenorhabditis elegans*, was evaluated by placement of a suspension of *C. elegans* nematodes in a medium containing a food source and a candidate nematicide at test rates of 5.0–1.25 ppm. One milliliter of a test medium consisting of 5 mg ampicillin, 10,000 units of mycostatin and 10 ml of a dense suspension of *Escherichia coli* per 100 ml of a buffer solution, was pipetted into each well of a 24-well microtiter plate. The *E. coli* act as the source of food for the *C. elegans* nematode. The candidate nematicides, in the appropriate concentration in dimethylsulfoxide, were added to the wells in 2.5 μl volumes. Each rate of application was replicated two to three times. After thorough mixing of the contents of each well, 50 to 100 μl of a nematode suspension in a buffer was added so that each well received 10–15 nematodes. After the nematodes were added the microtiter plates were incubated at 20° C. for 5–6 days. The effect of the candidate nematicide on the survival and the reproduction of *C. elegans* was then evaluated by comparison of the level of population development in the treated wells with that in untreated wells. Specific deleterious effects on population development, such as reduced egg hatch or molting disruption, were noted if they were evident.

Root-knot Nematode Tests were conducted by incorporation of the formulated candidate nematicide at rates varying from 10 to 0.312 ppm in nematode-infested soil. Soil previously infested with root-knot nematode eggs and larvae was treated with a candidate nematicide, then placed in 7.6 cm fiber pots. A cucumber or a tomato seedling was planted in each pot. The tests were evaluated approximately two-weeks post-treatment.

The results of the nematode tests for C. Elegans+- rootknot nematode are reported in Table II. In the results for C. Elegans, a "+" indicates the test compound produced at least a twenty percent inhibition of reproduction of C. Elegans and/or a twenty percent mortality rate at five ppm; a "−" indicates that the compound was inactive or only marginally active at 5 ppm. For rootknot nematode, a "+" indicates at least 20 percent control at an application rate in the range of 1.25 to 10 ppm, and a "−" indicates marginal or no control in that range.

Of particular interest as insecticides are Compound Nos. 18, 56, 59, 79, 81, 118, 137, 140 and 199. Compounds of particular interest as broad spectrum pesticides, e.g. as insecticides and nematicides, are Compound Nos. 56, 59, 79, 80, 118, 137, 140, 165, and 199. Compounds of particular interest as nematicides are Compound Nos. 3, 57, 64, 85, 118, 137, and 190.

The compounds of this invention are useful for control of pests which feed upon and/or damage the above ground or other portions of agricultural crops, and are particularly effective against insects such as aphids and loopers. In addition, they also show selective efficacy against soil borne insects and nematodes. Quite surprisingly, many of them also exhibit upward systemic activity as well.

In normal use, the compounds usually will not be employed free from admixture or dilution, but ordinarily will be used in a suitable formulated composition compatible with the method of application and comprising an insecticidally, acaricidally, or nematicidally effective amount of the compound. The compounds of this invention, like most pesticidal agents, may be blended with agriculturally acceptable surface-active agents and carriers normally employed for facilitating the dispersion of active ingredients, recognizing the accepted fact that the formulation and mode of application may affect the activity of the material. The present compounds may be applied, for example, as sprays, dusts, or granules to the area where pest control is desired, the type of application varying of course with the pest and the environment. Thus, the compounds of this invention may be formulated as granules of large particle size, as powdery dusts, as wettable powders, as emulsifiable concentrates, as solution, and the like.

Granules may comprise porous or nonporous particles, such as attapulgite clay or sand, for example, which serve as carriers for the present compounds. The granule particles are relatively large, a diameter of about 400–2500 microns typically. The particles are either impregnated with the compound of the invention from solution or coated with the compound, adhesive sometimes being employed. Granules generally contain 0.05–10%, preferably 0.5–5%, active ingredient.

Dusts are admixtures of the compounds, with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the compound. These finely divided solids have an average particle size of less than about 50 microns. A typical dust formulation contains 1 part of compound and 99 parts of talc.

The compounds of the present invention may be made into liquid concentrates by dissolution or emulsification in suitable liquids and into solid concentrates by admixture with talc, clays, and other known solid carriers used in the pesticide art. The concentrates are compositions containing about 5–50% active compound and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

A typical 50% wettable powder formulation would consist of 50.0% (wt/wt) of active ingredient, 22.0% attapulgite diluent, 22.0% kaolin diluent, and 6.0% sodium salts of sulfonated Kraft lignin emulsifier.

Typical carriers for solid concentrates (also called wettable powders) include fuller's earth, clays, silicas, and other highly absorbent, readily wetted inorganic diluents. A suitable solid concentrate formulation may contain 1.5 parts each of sodium lignosulfonate and sodium lauryl-sulfate as wetting agents, 25 parts of active compound and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the active compound with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

A typical 50 gram per liter emulsifiable concentrate formulation would consist of 5.90% (wt/wt) of a compound of the invention; as emulsifiers: 1.80% of a blend of the calcium salt of dodecylbenzene sulfonate and nonionic 6-molar ethylene oxide condensation product of nonylphenol, 2.70% of a blend of the calcium salt of dodecylbenzene sulfonate and a nonionic 30-molar ethylene oxide condensation product of nonylphenol, 1.50% of a nonionic paste of polyalkylene glycol ether; and 88.10% refined xylene solvent.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. The surfactive agent normally comprises about 1–15% by weight of the active ingredient.

Other useful formulations include simple solutions of the active ingredient in a solvent in which it is completely soluble at the desired concentration, such as acetone or other organic solvents.

An insecticidally, acaricidally, or nematicidally effective amount of the compound in an insecticidal, acaricidal, or nematicidal composition diluted for application is normally in the range of about 0.001% to about 8% by weight. Many variations of spraying and dusting compositions known in the art may be used by substituting the compounds of this invention into compositions known or apparent in the art.

The compositions of this invention may be formulated with other active ingredients, including other acaricides, nematicides, insecticides, fungicides, plant growth regulators, fertilizers, etc. In using the compositions to control pests, it is only necessary that an insecticidally or nematicidally effective amount of the compound be applied to the locus where control is desired. Such locus may, e.g., be the insect itself, plants upon which the insects feed, or the soil in which the pest resides for at least a portion of its life cycle. When the locus is soil, e.g., soil in which agricultural crops are or will be planted, the active compound may be applied to and optionally incorporated into the soil. For most applications, an insecticidally or nematicidally effective amount will be about 50 to 750 g per hectare, preferably 150 g to 500 g per hectare.

We claim:

1. A method for controlling pests which damage agricultural crops which comprises applying to the locus where control is desired an insecticidally, acaricidally, or nematically effective amount of a 2-fluoroethyl ether of the formula $R^1R^2{}_mAr((OCH_2CH_2F)_n$ in which:

Ar is phenyl and n is 1 to 3, or Ar is naphthyl and n is 1 or 2, or Ar is phenylmethyl, (alkyl)(phenyl)-methyl, diphenylmethyl, or naphthylmethyl and n is 1; and (a) m is 0 and $R^1$ is selected from halogen, halomethyl, hydroxymethyl, fluoroethoxymethyl, alkoxy, difluoromethoxy, hydroxy, phenoxy, phenyl, fluoroethoxyphenyl, with the proviso that Ar is other than naphthyl when $R^1$ is hydroxy; or (b) m is 1, $R^1$ is selected from alkyl, and halogen, and $R^2$ is halogen or (c) m is 2–5, and $R^1$ methyl is or halogen and $R^2$ is halogen.

2. A pesticidal composition comprising an agriculturally acceptable vehicle, diluent, or carrier in admixture with an insecticidally acaricidally or nematicidally effective amount of a 2-fluoroethyl ether of the formula $R^1R^2{}_mAr(OCH_2CH_2F)_n$ in which:

Ar is phenyl and n is 1 to 3, or Ar is naphthyl and n is 1 or 2, or Ar is phenylmethyl, (alkyl)(phenyl)-methyl, diphenylmethyl, or naphthylmethyl and n is 1; and m is 0 and $R^1$ is selected from trifluoromethyl, fluoroethyoxymethyl, difluoromethoxy, phenoxy, phenyl, fluoroethoxyphenyl, with the proviso that Ar is other than naphthyl when $R^1$ is methylthio; or m is 1, $R^1$ is selected from alkyl, and halogen, and $R^2$ is halogen with the proviso that $R^1$ is other than alkyl when Ar is phenyl and n is 1; or m is 2–5, $R^1$ is methyl or halogen and $R^2$ is halogen.

3. An insecticidal or nematicidal 2-fluoroethyl ether of the formula $R^1R^2{}_mAr(OCH_2CH_2F)_n$ in which:

Ar is phenyl and n is 1 to 3, or Ar is naphthyl and n is 1 or 2, or Ar is phenylmethyl, (alkyl)(phenyl)-methyl, diphenylmethyl, or naphthylmethyl and n is 1; and m is 0 and $R^1$ is selected from trifluoromethyl, fluoroethoxymethyl, difluoromethoxy, phenoxy, phenyl, fluoroethoxyphenyl, with the proviso that Ar is other than naphthyl when $R^1$ is methylthio; or m is 1, $R^1$ is selected from alkyl, halogen, and $R^2$ is halogen, with the proviso that $R^1$ are other than alkyl when Ar is phenyl and n is 1; or m is 2–5, $R^1$ is methyl or halogen and $R^2$ is halogen.

4. A method for controlling pests which damage agricultural crops which comprises applying to the locus where control is desired an insecticidally, acaricidally, or nematicidally effective amount of a 2-fluoroethyl ether selected from the group consisting of:

2-Chlorophenyl 2-fluoroethyl ether;
2-Bromophenyl 2-fluoroethyl ether;
2-Fluoroethyl 2-iodophenyl ether;
2-Fluoroethyl 2-hydroxymethylphenyl ether;
2-Fluoroethyl ([1,1'-biphenyl]-2-yl) ether;
2-Fluoroethyl 2-methoxyphenyl ether;
2-Fluoroethyl 2-difluoromethoxyphenyl ether;
2-Fluoroethyl 3-fluorophenyl ether;
3-Chlorophenyl 2-fluoroethyl ether;
3-Bromophenyl 2-fluoroethyl ether;
2-Fluoroethyl 3-iodophenyl ether;
2-Fluoroethyl 3-trifluoromethylphenyl ether;
2-Fluoroethyl 3-hydroxyphenyl ether;
2-Fluoroethyl 3-methoxyphenyl ether;
2-Fluoroethyl 3-difluoromethoxyphenyl ether;
2-Fluoroethyl 3-phenoxyphenyl ether;
4-Bromophenyl 2-fluoroethyl ether;
2-Fluoroethyl 4-iodophenyl ether;
2-Fluoroethyl 4-trifluoromethylphenyl ether;
2-Fluoroethyl 4-hydroxymethylphenyl ether;
2-Fluoroethyl ([1,1'-biphenyl]-4-yl) ether;
4,4'-di(2-Fluoroethyoxy)-[1,1'-biphenyl];
4-(2-Fluoroethoxymethyl)phenyl 2-fluoroethyl ether;
2-Fluoroethyl 4-hydroxyphenyl ether;
2-Fluoroethyl 4-methoxyphenyl ether;
2-Fluoroethyl 4-pentoxyphenyl ether;
2-Fluoroethyl 4-difluoromethoxyphenyl ether;
2-Fluoroethyl 4-phenoxyphenyl ether;
2-Fluoroethyl, 2,4-difluorophenyl ether;
2-Fluoroethyl 2,6-difluorophenyl ether;
4-Bromo-2-chlorophenyl 2-fluoroethyl ether;
4-Chloro-3-methylphenyl 2-fluoroethyl ether;
2-Bromo-4-methylphenyl 2-fluoroethyl ether;
2-Fluoroethyl pentafluorophenyl ether;
1,2-Di(2-fluoroethoxy)benzene;
2,3-Di(2-fluoroethoxy)toluene;
1,2-Di(2-fluoroethoxy)-3-(1-methylethyl)benzene;
3-Bromomethyl-1,2-di(2-fluoroethoxy)benzene;
1,2-Di(2-fluoroethoxy)-3-methoxybenzene;
4-Bromo-1,2-di(2-fluoroethoxy)benzene;
3,4-Di(2-fluoroethoxy)toluene;
1,2-Di(2-fluoroethoxy)-4-(1,1-dimethylethyl)benzene;
1,3-Di(2-fluoroethoxy)benzene;
4-Bromo-1,3-di(2-fluoroethoxy)benzene;
2,4-di(2-fluoroethoxy)toluene;
3,5-Di(2-fluoroethoxy)toluene;
1,3-Di(2-fluoroethoxy)-5-pentylbenzene;
1,3-Di(2-fluoroethoxy)-5-methoxybenzene;
1,4-Di(2-fluoroethoxy)benzene;
2-Bromo-1,4-di(2-fluoroethoxy)benzene;
1,4-Di(2-fluoroethoxy)-2-(1,1-dimethylethyl)benzene;
1,2,3-Tri(2-fluoroethoxy)benzene;
1,3,5-Tri(2-fluoroethoxy)benzene;
2-(2-Fluoroethoxy)-1-hydroxymethylnaphthalene;
6-Bromo-2-(2-fluoroethoxy)naphthalene;
2-(2-Fluoroethoxy)-6-(1-methyethyl)naphthalene;
1,3-Di(2-fluoroethoxy)naphthalene;
1,4-Di(2-fluoroethoxy)naphthalene;
1,5-Di(2-fluoroethoxy)naphthalene;
1,6-Di(2-fluoroethoxy)naphthalene;
1,7-Di(2-fluoroethoxy)naphthalene;
2,3-Di(2-fluoroethoxy)naphthalene;
2,6-Di(2-fluoroethoxy)naphthalene;
2,7-Di(2-fluoroethoxy)naphthalene;
2-Fluoroethyl benzyl ether;
2-Fluorobenzyl 2-fluoroethyl ether;
2-Chlorobenzyl 2-fluoroethyl ether;
2-Bromobenzyl 2-fluoroethyl ether;
2-Fluoroethyl 2-trifluoromethylbenzyl ether;
2-Fluoroethyl 2-methoxylbenzyl ether;

3-Fluorobenzyl 2-fluoroethyl ether;
3-Chlorobenzyl 2-fluoroethyl ether;
3-Bromobenzyl 2-fluoroethyl ether;
2-Fluoroethyl 3-methylbenzyl ether;
2-Fluoroethyl 3-methoxybenzyl ether;
4-Fluorobenzyl 2-fluoroethyl ether;
4-Chlorobenzyl 2-fluoroethyl ether;
4-Bromobenzyl 2-fluoroethyl ether;
2-Fluoroethyl 4-methylbenzyl ether;
2-Fluoroethyl 4(1-methylethyl)benzyl ether;
2-Fluoroethyl 4-trifluoromethylbenzyl ether;
2-Fluoroethyl 4-methoxybenzyl ether;
2,6-Dichlorobenzyl 2-fluoroethyl ether;
1,2-Di(2-fluoroethoxymethyl)benzene;
2-Fluoroethyl pentafluorobenzyl ether;
2-Fluoroethyl diphenylmethyl ether;
1-(2-Chlorophenyl)ethyl 2-fluoroethyl ether;
1-(2-Chlorophenyl)-2-propyl 2-fluoroethyl ether;
2-Chloro-α-phenylbenzyl 2-fluoroethyl ether;
3,4-Dichlorobenzyl 2-fluoroethyl ether;
3,5-Dichlorobenzyl 2-fluoroethyl ether;
2,3,5-Trichlorobenzyl 2-fluoroethyl ether;
2,3,5,6-Tetrafluoro-4-methylbenzyl 2-fluoroethyl ether;
1-(2-fluoroethoxy)naphthalene;
4-Chloro-1-(2-fluoroethyoxy)naphthalene;
4-Bromo-1-(2-fluoroethoxy)naphthalene;
1-(2-Fluoroethoxy)-4-iodonaphthalene;
1-(2-Fluoroethoxy)-4-methylethyl)naphthalene;
1-(2-Fluoroethoxy)-4-(1-methylethyl)naphthalene;
1-(2-Fluoroethoxy)-4-cyclopentylnaphthalene;
1-(2-Fluoroethoxy)-4-(2-fluoroethoxymethyl)naphthalene;
1-(2-Fluoroethoxy)-4-methoxynaphthalene;
1-(2-Fluoroethoxy)-4-(1-methylethoxy)naphthalene;
4-(2-Fluoroethoxy)naphthaldehyde;
1-(2-Fluoroethoxy)-4-phenylnaphthalene;
1-(2-Fluoroethoxymethyl)naphthalene;
4-Fluoro-1-(2-fluoroethoxymethyl)naphthalene;
1-(2-Fluoroethoxymethyl)-4-methoxynaphthalene; and 5. A pesticidal composition comprising an insecticidally or nematicidally effective amount of a 2-fluoroethyl ether in admixture with an agriculturally acceptable vehicle, diluent, or carrier in which said 2-fluoroethyl ether is selected from the group consisting of:
2-Fluoroethyl ([1,1'-biphenyl]-2-yl) ether;
2-Fluoroethyl 2-difluoromethoxyphenyl ether;
2-Fluoroethyl 3-trifluoromethylphenyl ether;
2-Fluoroethyl 3-difluoromethoxyphenyl ether;
2-Fluoroethyl 3-phenoxyphenyl ether;
2-Fluoroethyl 4-trifluoromethylphenyl ether;
2-Fluoroethyl ([1,1'-biphenyl]-4-yl) ether;
4,4'-di(2-Fluoroethoxy)-[1,1'-biphenyl];
4-(2-Fluoroethoxymethyl)-phenyl 2-fluoroethyl ether;
2-Fluoroethyl 4-difluoromethoxyphenyl ether;
2-Fluoroethyl 4-phenoxyphenyl ether;
2-Fluoroethyl 2,4-difluorophenyl ether;
2-Fluoroethyl 2,6-difluorophenyl ether;
4-Bromo-2-chlorophenyl 2-fluoroethyl ether;
2-Fluoroethyl pentafluorophenyl ether;
1,2-Di(2-fluoroethoxy)benzene;
2-Fluoroethyl 2-trifluoromethylbenzyl ether;
2-Fluoroethyl 4-trifluoromethylbenzyl ether;
2,6-Dichlorobenzyl 2-fluoroethyl ether;
1,2-Di(2-fluoroethyoxymethyl)benzene;
2-Fluoroethyl pentafluorobenzyl ether;
2-Fluoroethyl diphenylmethyl ether;
1-(2-Chlorophenyl)ethyl 2-fluoroethyl ether;
1-(2-Chlorophenyl)-2-methylpropyl 2-fluoroethyl ether;
2-Chloro-α-phenylbenzyl 2-fluoroethyl ether;
3,4-Dichlorobenzyl 2-fluoroethyl ether;
3,5-Dichlorobenzyl 2-fluoroethyl ether;
2,3,5-Trichlorobenzyl 2-fluoroethyl ether;
2,3,5,6-Tetrafluoro-4-methylbenzyl -2-fluoroethyl ether;
1-(2-Fluoroethoxy)-4-(2-fluoroethoxymethyl)naphthalene;
1-(2-Fluoroethoxy-4-phenylnaphthalene.

6. A 2-fluoroethyl ether, selected from the group consisting of:
2-Fluoroethyl ([1,1'-biphenyl]-2-yl) ether;
2-Fluoroethyl 2-difluoromethoxyphenyl ether;
2-Fluoroethyl 3-trifluoromethylphenyl ether;
2-Fluoroethyl 3-difluoromethoxyphenyl ether;
2-Fluoroethyl 3-phenoxyphenyl ether;
2-Fluoroethyl 4-trifluoromethylphenyl ether;
2-Fluoroethyl ([1,1'-biphenyl]-4-yl) ether;
4,4'-di(2-Fluoroethoxy)-[1,1'-biphenyl];
4-(2-Fluoroethoxymethyl)phenyl 2-fluoroethyl ether;
2-Fluoroethyl 4-difluoromethoxyphenyl ether;
2-Fluoroethyl 4-phenoxyphenyl ether;
2-Fluoroethyl 2,4-difluorophenyl ether;
2-Fluoroethyl 2,6-difluorophenyl ether;
4-Bromo-2-chlorophenyl 2-fluoroethyl ether;
2-Fluoroethyl pentafluorophenyl ether;
1,2-Di(2-fluoroethoxy)benzene;
2-Fluoroethyl 2-trifluoromethylbenzyl ether;
2-Fluoroethyl 4-trifluoromethylbenzyl ether;
2,6-Dichlorobenzyl 2-fluoroethyl ether;
1,2-Di(2-fluoroethoxymethyl)benzene;
2-Fluoroethyl pentafluorobenzyl ether;
2-Fluoroethyl diphenylmethyl ether;
1-(2-Chlorophenyl)ethyl 2-fluoroethyl ether;
1-(2-Chlorophenyl)-2-methylpropyl 2-fluoroethyl ether;
2-Chloro-α-phenylbenzyl 2-fluoroethyl ether;
3,4-Dichlorobenzyl 2-fluoroethyl ether;
3,5-Dichlorobenzyl 2-fluoroethyl ether;
2,3,5-Trichlorobenzyl 2-fluoroethyl ether;
2,3,5,6-Tetrafluoro-4-methybenzyl 2-fluoroethyl ether;
1-(2-Fluoroethoxy)-4-(2-fluoroethyoxymethyl)naphthalene;
1-(2-Fluoroethoxy)-4-phenylnaphthalene.

* * * * *